(12) United States Patent
Wu et al.

(10) Patent No.: US 9,241,962 B2
(45) Date of Patent: Jan. 26, 2016

(54) **WATER EXTRACT OF *ANTRODIA CAMPHORATA* FOR IMMUNOSTIMULATORY EFFECT AND PREPARATION METHOD THEREOF**

(71) Applicant: Kaohsiung Medical University, Kaohsiung (TW)

(72) Inventors: Yang-Chang Wu, Kaohsiung (TW); Mei-Chin Lu, Pingtung County (TW); Fang-Rong Chang, Kaohsiung (TW); Ying-Chi Du, Chiayi (TW); Tung-Ying Wu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 14/577,605

(22) Filed: Dec. 19, 2014

(65) Prior Publication Data

US 2015/0104481 A1    Apr. 16, 2015

Related U.S. Application Data

(62) Division of application No. 12/552,115, filed on Sep. 1, 2009, now abandoned.

(30) Foreign Application Priority Data

Mar. 4, 2009 (TW) .............................. 98107047 A

(51) Int. Cl.
*A61K 36/07* (2006.01)
*A61K 39/39* (2006.01)
*C12N 5/0784* (2010.01)
*A61K 39/00* (2006.01)

(52) U.S. Cl.
CPC ............... *A61K 36/07* (2013.01); *A61K 39/39* (2013.01); *C12N 5/0639* (2013.01); *A61K 2039/60* (2013.01); *C12N 2500/74* (2013.01)

(58) Field of Classification Search
CPC .................................................. A61K 36/074
USPC .................................................. 424/195.16
See application file for complete search history.

(56) References Cited

U.S. PATENT DOCUMENTS

| 2003/0113297 A1 | 6/2003 | Chen et al. |
| 2003/0148517 A1 | 8/2003 | Chen et al. |
| 2006/0052337 A1 | 3/2006 | Hattori et al. |
| 2008/0312334 A1 | 12/2008 | Liu et al. |
| 2010/0227404 A1 | 9/2010 | Wu et al. |

FOREIGN PATENT DOCUMENTS

| TW | 591110 | 6/2004 |
| TW | I279439 | 4/2007 |
| TW | 200819136 A | 5/2008 |
| TW | I299665 | 8/2008 |

OTHER PUBLICATIONS

Jun-Jen Liu et al. "Antitumor effects of the partially purified polysaccharides from Antrodia camphorata and the mechanism of its action", Toxicology and Applied Pharmacology 201 (2004) 186-193.*

Mei-Chin Lu et al. "Immunostimulatory effect of Antrodia camphorata extract on functional maturation of dendritic cells", Food Chemistry 113 (2009) 1049-1057.*

Banchereau et al., "Dendritic cells: controllers of the immune system and a new promise for immunotherapy," Ann. N.Y. Acad. Sci. (2003), 987: 180-187.

Chen et al., "Chemical characterization and anti-inflammatory effect of polysaccharides fractionated from submerge-cultured Antrodia camphorata mycelia," J. Agric. Food Chem. (2007), 55(13): 5007-5012.

Chen, "Studies on the Immunomodulatory Properties of Chinese Herbal Formulas and the Anti-Tumor Effects of Antrodia cinnamomea Fruiting Bodies," (2007). (English Abstract provided).

Chen et al, "Unique Formosan Mushroom Antrodia camphorata Differentially Inhibits Androgen-Responsive LNCaP and -Independent PC-3 Prostate Cancer Cells," Nutrition and Cancer, 57(1), pp. 111-121 (2007).

Hart et al., "Dendritic cells: Unique leukocyte populations which control the primary immune response," Blood (1997), 90(9): 3245-3287.

Hsu, "Preparation of $(1\rightarrow 3)$-$\beta$-D-glucan from submerged cultivation of Antrodia camphorate," paragraph 2 of p. 6; Table 1 of p. 7; p. 17; Fig. 6 of p. 18; 2-2-2 of p. 23 and 2-2-3 of p. 24 (Nov. 7, 2006). (English Abstract provided).

Jen-Leun et al. "Antioxidant Properties of Methanolic Extracts from two kinds of Antrodia Camphorata Mycelium" (Food Chemistry 86, pp. 25-31 (2004).

Lin et al., "Polysaccharide purified from Ganoderma lucidum induces gene expression changes in human dendritic cells and promotes T helper 1 immune response in BALB/c mice," Mol. Pharmacol. (2006), 70(2): 637-644.

Liu et al., "antitumor effects of the partially purified polysaccharides from Antrodia camphorata and the mechanism of its action," Toxicol. Appl. Pharmacol. (2004), 201(2): 186-193.

Lu et al., "Fermented Antrodia cinnamomea Extract Protects Rat PC12 Cells from Serum Deprivation-Induced Apoptosis: The Rode of the MAPK Family," Journal of Agricultural and Food Chemistry 56, pp. 865-874 (2008).

Lu et al., "Immunostimulatory effect of Antrodia camphorata extract on functional maturation of dendritic cells," Food Chem. (2009), 113(4): 1049-1057 (online available on Sep. 5, 2008 and published on Apr. 15, 2009).

Martinez et al., "Extracellular acidosis triggers the maturation of human dendritic cells and the production of IL-12," J. Immunol. (2007), 179(3): 195.

* cited by examiner

*Primary Examiner* — Chris R Tate
*Assistant Examiner* — Deborah Davis
(74) *Attorney, Agent, or Firm* — Volpe and Koenig, P.C.

(57) ABSTRACT

A preparation method for a water extract of the fruiting body of *Antrodia camphorata* (ACW) is provided. The method includes steps of: (a) providing the fruiting body; and (b) boiling the fruiting body in water to obtain the water extract. This polysaccharide-rich water extract from *A. camphorata* induces the maturation of dendritic cells, enhances T cell proliferation and INF-γ production, and polarizes them toward the Th1 pathway. ACW can be effectively applied in cancer immunotherapy.

5 Claims, 12 Drawing Sheets

WATER EXTRACT OF *ANTRODIA CAMPHORATA* FOR IMMUNOSTIMULATORY EFFECT AND PREPARATION METHOD THEREOF

CROSS REFERENCE TO RELATED APPLICATIONS

This application is a divisional of U.S. patent application Ser. No. 12/552,115, which was filed Sep. 1, 2009, and claims the benefit of Taiwanese Patent Application Serial No. 098107047, which was filed Mar. 4, 2009, all of which are incorporated by reference as if fully set forth.

FIELD OF INVENTION

The present invention relates to an extract of a fruiting body of *Antrodia camphorata* and the preparing method thereof. In particular, the present invention relates to a water extract of a fruiting body of *A. camphorata* (ACW) and the preparing method thereof, and the water extract has immunostimulatory effect on dendritic cells (DCs).

BACKGROUND OF THE INVENTION

*Antrodia camphorata* (AC) is an endemic mushroom in Taiwan and grows in the internal heartwood (or the dark/humid wood surface) of the particular *Cinnamomum kanehirai* in 400 to 2000 meters altitude. Therefore, it is uneasily to find out the wide fruiting body of AC or identify the morphological appearance of this Aphyllophorales fungus. In addition, the price of AC is still high due to their biologically active components having potential pharmaceutical value.

The fruiting body of AC cannot be easily harvested and be artificially cultured. In addition, mycelia products of AC are popular in the market and announce to own anticancer activity, reduced cancer therapy-related symptoms and other side effects, anti-oxidation, anti-hypersensitivity and immunostimulatory effects.

In immune response, the stimulated and activated dendritic cells (DCs) emerge as the antigen presenting cells (APCs) to present antigens toward unprimed T lymphocytes (Hart et al., 1997). The maturation and functions of DCs are tightly regulated by cytokines and costimulatory signals (Martinez et al., 2007). Recent research is found that the DC-based immunotherapy is able to apply in treating malignancies (Banchereau et al., 2003). The maturation process is the main function of DCs and enables one cell to perform different, highly specialized functions sequentially. Many stimuli, including lipopolysaccharide (LPS), can induce the maturation process of DCs in vitro.

In the present researches, polysaccharides produced from this medical mushroom can be new pharmaceuticals for inducing the maturation and activation of DCs. Therefore, when searching for new cancer immunotherapy agents, the edible and medicinal fungi being used for cancer treatment in folk medicine are promising candidates, wherein AC is the most popular one.

Taiwan Patent No. 1299665 discloses an extract of AC and the preparing method thereof, wherein polysaccharide is obtained from extraction of mycelia of *Taiwanofungus camphoratus* with ethanol so as to inhibit the activity of matrix metalloproteinases. However, the extraction is not performed with the fruiting body of AC, and the product also cannot inhibit the growth of cancer cells. Taiwan Patent No. 1279439 discloses inoculate obtained from incubating mycelia of AC by adjusting the pH value at incubation, but there is not extraction method disclosed. Taiwan Patent No. 591110 discloses that γ-aminobutyric acid is extracted from the lyophilized mycelia of AC with water or organic solvents. However, the above-mentioned inventions do not disclose any product of the wild fruiting body of AC extracted with water or organic solvent, and the effect of ACW on DCs is not identified in the immune response.

It is therefore attempted by the applicant to deal with the above situation encountered in the prior art.

SUMMARY OF THE INVENTION

The water extract of the fruiting body of wild *A. camphorata* (abbreviated as ACW) is obtained by extracting the fruiting body of AC with water, and ACW can effectively induce immune response and stimulate DCs. ACW is further sequentially extracted with ethyl acetate, ethanol and water to obtain an ethyl acetate (ACW-EA), an ethanol extract (ACW-E) and a second water extract (ACW-W) of the fruiting body of AC. It can be identified from the above three extracts that polysaccharide can induce maturation of DCs and activate T cells.

In accordance with the first aspect of the present invention, a fractionation extract of the fruiting body of *Antrodia camphorata* (AC) is provided. The fractionation extract includes at least one characteristic of: (1) causing first signals of carbohydrate on a first $^1$H nuclear magnetic resonance (NMR) spectrum; and (2) causing a plurality of hydrogen signals of anomeric carbons of the polysaccharides on a second $^1$H NMR spectrum.

Preferably, the first signals have the first chemical shift ranged between 3.0 and 5.5, and the plurality of hydrogen signals have second chemical shifts at 4.44, 4.46, 4.91, 5.00 and 5.15 respectively.

Preferably, the fractionation extract is a second water extract fractionized from a water extract of the fruiting body of the *Antrodia camphorata*.

In accordance with the second aspect of the present invention, a method for preparing a water extract of the fruiting body of AC is provided. The method includes steps of: (a) providing the fruiting body; and (b) boiling the fruiting body in the water to obtain the water extract.

Preferably, the step (a) further includes a step (a1) of grinding the fruiting body as a powder, and the step (b) further includes a step (b1) of refluxing the water after the boiling step.

Preferably, the water extract has a precipitate therein, and the method further includes a step (c) of removing the precipitate from the water extract.

Preferably, the step (c) is performed by at least one of treatments of filtering the water extract and centrifuging the water extract.

Preferably, the step (c) further includes a step (d) of extracting the water extract with at least one organic solvent to obtain an organic solvent extract.

Preferably, the at least one organic solvent has ethyl acetate and ethanol, and the step (d) further includes steps of: (d1) extracting the water extract with ethyl acetate to obtain an ethyl acetate extract and a first residue; and (d2) extracting the first residue with ethanol to obtain an ethanol extract and a second residue.

Preferably, the step (d2) further includes a step (d3) of extracting the second residue with water to obtain a second water extract.

In accordance with the third aspect of the present invention, a method for maturating a cell is provided. The method includes a step of administrating the cell with a water extract as mentioned above.

Preferably, the cell is an immature dendritic cell (DC).

Preferably, the cell expresses at least one protein after the administration with the water extract, and the at least one protein is one selected from a group consisting of a CD86, a human leukocyte antigen (HLA)-DR and a combination thereof.

Preferably, the method further includes a step of providing a second cell, wherein the cell expresses a cytokine after the administration with the water extract, and the cytokine induces the second cell to express a second cytokine.

Preferably, the cytokine includes interleukin-12 (IL-12), the second cell is helper T cell, and the second cytokine is interferon-gamma (INF-γ).

Preferably, the cell progresses a cell migration induced by the water extract.

Preferably, the cell expresses at least one protein after the administration with the water extract, and the at least one protein is one selected from a group consisting of a Bax, a Bcl-2, a nuclear factor kappa B (NFκB) p65, a phosphorylated p38 (p-p38), a phosphorylated c-Jun N-terminal kinase (p-JNK), a phosphorylated protein kinase B (p-Akt), a phosphorylated extracellular signal-regulated kinase (p-ERK) and a combination thereof.

Preferably, the cell is induced by the water extract to go into the htephosphatidylinositol-3 kinase/protein kinase B (PI3K/Akt) pathway and/or the mitogen-activated protein kinase (MAPK) pathway.

The above objectives and advantages of the present invention will become more readily apparent to those ordinarily skilled in the art after reviewing the following detailed descriptions and accompanying drawings, in which:

BRIEF DESCRIPTION OF THE DRAWINGS

FIG. 12(A) and FIG. 12(B) respectively are the diagrams showing protein expressions of signaling transduction pathway of the ACW-stimulated DCs, wherein FIG. 12(A) shows Bax, Bcl-2 and p65, and FIG. 12(B) shows p-ERK, ERK, p-p38, p38, p-JNK, JNK and p-Akt.

DETAILED DESCRIPTION OF THE PREFERRED EMBODIMENT

Figure 1:
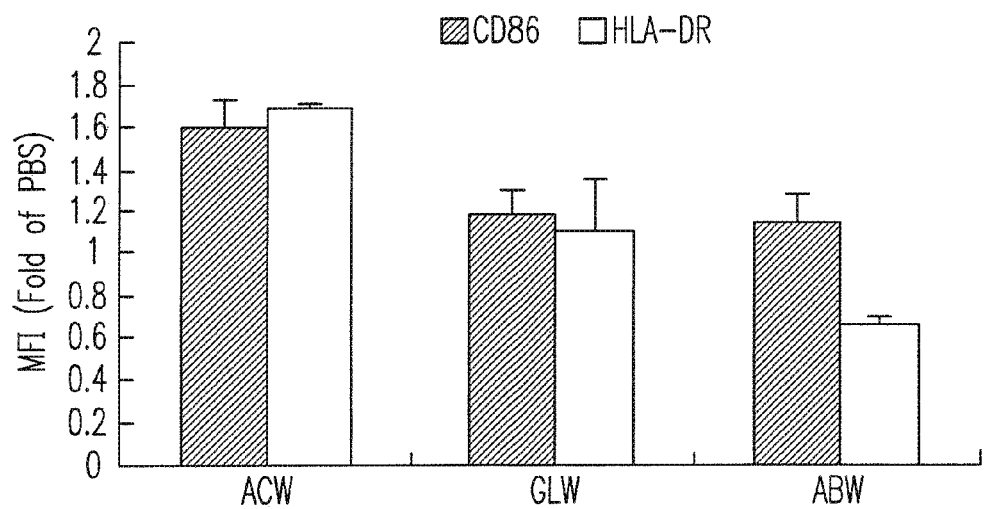
FIG. 1 is a diagram showing expressions of CD86 and HLA-DR after immatured DCs (ImDCs) are stimulated with ACW, GLW and ABW respectively.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

BIOLOGICAL EXPERIMENTS

Experiment 1

Water Extracts Respectively Extracted from Fruiting Bodies of *A. camphorate, Ganoderma lucidum* and *Agaricus blazei*

In accordance with the method for preparing polysaccharide in the literature (Liu et al., 2004), the dried fruiting bodies of AC, *G. lucidum* and *A. blazei* were grounded as fine powder, then were boiled to reflux at a ratio of 1:10 (w/v) for 8 hours. Next, the supernatants were filtered to remove the precipitate at 3,000 rpm for 30 minutes, then were lyophilized. The obtained water extracts of AC, *G. lucidum* and *A. blazei* (sequentially abbreviated as ACW, GLW and ABW) were preserved at −70° C. In addition, the amounts of carbohydrate thereof were determined using phenol-sulfuric acid method (Chen et al., 2007).

Experiment 2

Further Extraction and Fractionation of ACW

ACW (216.4 mg) was extracted with solvents (sequentially as ethyl acetate, ethanol and water) of increasing polarities to obtain three different extracts, 8.9% (19.3 mg) of ethyl acetate extract (ACW-EA), 38.5% (83.3 mg) of ethanol extract (ACW-E) and 52.6% (113.8 mg) of a second water extract (ACW-W). Percentage is referred to the weight percentage of ACW, and weight is referred to the dry material extracted. The amount of carbohydrate in each extract was determined using phenol-sulfuric acid method (Chen et al., 2007), and the spectrum characteristics therein were analyzed with NMR.

Experiment 3

NMR Method

The above-mentioned extracts were solved in deuterium solvents such as dideuterium monoxide ($D_2O$), pyridine-D5 ($C_5D_5N$) and so on, and then $^1$H NMR spectra were recorded on a Varian Unity Inova-600 MHz NMR. Chemical shift was reported in parts per million (ppm, d).

Experiment 4

Preparation of Human T Cells and DCs

The preparation method of DCs was mainly prepared and modified from Lin et al, 2006. First, peripheral blood mononuclear cells (PBMCs) were obtained from 12 healthy donors by centrifugation with the Ficoll-Hypaque (Amersham Bioscience, Uppsala, Sweden) density gradient centrifugation. PBMCs were cultured in RPMI 1640 medium supplemented with 10% fetal calf serum, 1 mM L-glutamin, 100 µg/ml streptomycin and 100 U/ml penicillin for 2 hours. The nonadherent cells were removed, and the T cells were purified by nylon wool separation, as the source of mononuclear T lymphocytes. T cells were loaded into the column and the eluted nonadherent cell fraction was rich in T cells. As determined by FACS, the resulting cell population was 80% T cells with a high expression of CD3. The adherent cells were cultured for 6 days in RPMI 1640 medium with 50 ng/ml of granulocyte-macrophage colony-stimulating factor (GM-CSF) and interleukin-4 (IL-4). Half of the culture medium was replaced by fresh medium containing growth factors every 2 to 3 days. On day six of culture, cells were collected and incubated with anti-CD11C$^+$ microbeads in conjunction with the mini MACs system by following the manufacturer's instructions (Becton Dickinson, Mountain View, Calif.). The CD11C-positive cells were above 90% pure to obtain ImDCs. ImDCs were further treated with phosphate buffered saline (PBS), LPS (100 ng/ml) and different doses of ACW for an additional 2 days and then assessed by flow cytometry.

Experiment 5

Mixed Allogenic T Lymphocyte Reaction (MLR)

The treated DCs were pretreated with 25 ng/ml of mitomycin C at 37° C. for 30 minutes and subsequently washed three times with culture medium before plating. The DCs were mixed with T cells at a concentration of 1:10 and 1:20. Cells were cultured for five days on 96-well flat-bottom plates and subsequently pulsed with 20 µl of WST-1 (2-(4-iodophenyl)-3-(4-nitrophenyl)-5-(2,4-disulfophenyl)-2H-tetrazolium, Roche, Germany) during the last 4 hours of culture. The absorbance of measuring wavelength (450 nm) and the reference wavelength (650 nm) were measured for T cell proliferation. All samples were measured against a background control. Cell culture supernatants were collected and analyzed for IL-4 and IFN-γ by enzyme-linked immunosorbent assay (ELISA).

Experiment 6

Immunofluorescence and Flow Cytometry

For phenotypic analysis, DCs were stained in PBS using fluorochrome-conjugated or isotype-matched control antibodies for 30 minutes at 37° C. The cells were analyzed by flow cytometry using a FACScalibur flow cytometer and Cell Quest software (Becton Dickinson, Mountain View, Calif.).

Experiment 7

Assays for Cytokines

Levels of IL-12, IL-10, IFN-γ and IL-4 in the culture supernatants from DCs or T cells were evaluated by using highly sensitive human cytokine assay kits (R&D Systems, Minneapolis, USA) according to the manufacturer's instructions.

Experiment 8

Migration Experiments

Chemotaxis of DCs was measured by the migration through a polycarbonate filter with 8 µm pore size in transwell chambers. First, DCs were treated for 48 hours with LPS, 25 and 50 µg/ml of ACW and assayed for migration. The lower chambers of transwell plates were filled with 500 µl serum-free medium with or without $2 \times 10^6$ T lymphocytes/ml. DCs ($1 \times 10^5$ cells in 0.1 ml) resuspended in serum-free medium were deposited in the upper chambers of the transwell plates and allowed to migrate for 3 hours at 37° C. in 5% CO2. The numbers of migrating DCs harvested from the lower chambers were counted by flow cytometry (60 second counts).

Experiment 9

Western Blot Analysis

DCs were stimulated with or without LPS or indicated doses of ACW, then lysed with RIPA Reagent (140 mM NaCl, 10 mM EDTA (2-[2-(Bis(carboxymethyl)amino)ethyl-(carboxymethyl)amino]acetic acid), 10% glycerol, 1% Nonidet P-40, 20 mM Tris (pH 7.0), 1 µM pepstatin, 1 µg/ml aprotinin, 1 µg/ml leupeptin and 1 mM sodium orthovanadate) and protein concentrations of the extracts were measured by BCA assay (Pierce, Rockford, Ill.). Twenty micrograms of protein was loaded per lane, subjected to sodium dodecyl sulfate-polyacrylamide gel electrophoresis (SDS-PAGE), transferred onto nitrocellulose membranes. Membranes were probed with primary antibodies and then incubated with appropriate horseradish peroxidase (HRP)-coupled secondary antibodies, and protein bands were visualized using LumiGLo reagent (Pierce).

Experiment 10

Inhibition of MAPKs and PI3K/Akt Activation

To examine the signal transduction pathways involved in the effects of ACW on DC maturation, DCs were pretreated at 37° C. with ERK inhibitor PD98059 (25 µM), JNK inhibitor SP600125 (25 µM), p38 MAPK inhibitor SB203580 (25 µM) or PI3K/Akt inhibitor LY294002 (25 µM) for 2 hours before stimulation with ACW. After 2 days, phenotyping characteristics of DCs and IL-12 production in the supernatants of DCs were analyzed.

Experiment 11

Statistical Analysis

Statistical analysis was performed using Student's t test. A value of $p<0.05$ was considered significant.

Experiment Results

Figure 2:
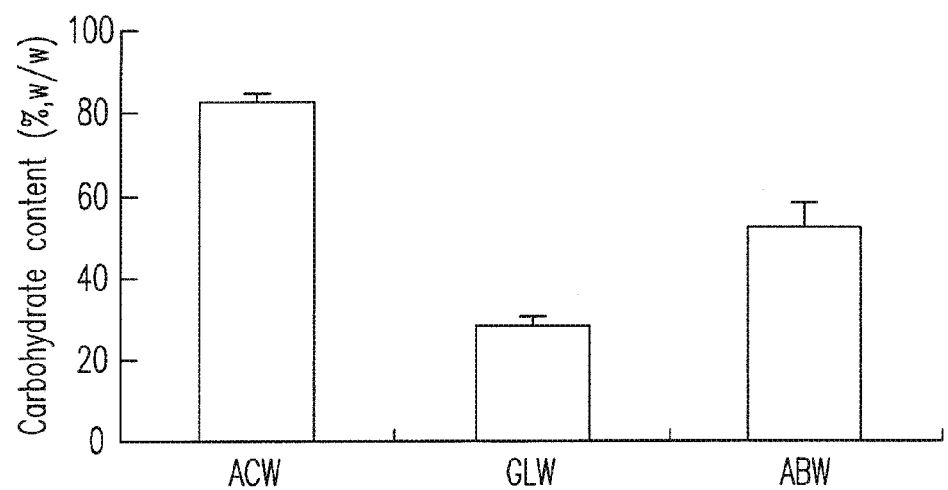
FIG. 2 is a diagram showing the carbohydrate contents of ACW, GLW and ABW.

1. Immunostimulatory Effect of ACW on the Phenotypic Maturation of DCs Compared with the Effects of GLW and ABW To compare the effect of polysaccharides of the respective edible and medicinal fungi on the maturation of DCs, ImDCs are cultured with ACW, GLW and ABW respectively, and expressions of costimulatory molecules, CD86 and HLA-DR, are analyzed with flow cytometry. Please refer to FIG. 1, which is a diagram showing expressions of CD86 and HLA-DR after ImDCs are stimulated with ACW, GLW and ABW respectively. Mean fluorescence intensity (MFI) for each treatment is expressed as a fold increase over PBS. It can be known from FIG. 1 that GLW- or ABW-treated DCs do not show a significant increase in phenotypic maturation as do by ACW-treated DCs. The carbohydrate of these extracts are estimated by phenol-sulfuric acid method, and the carbohydrate content of ACW is found to be 82.6% more than those of GLW (52.3%) and ABW (28.3%) (FIG. 2).

Figure 3:
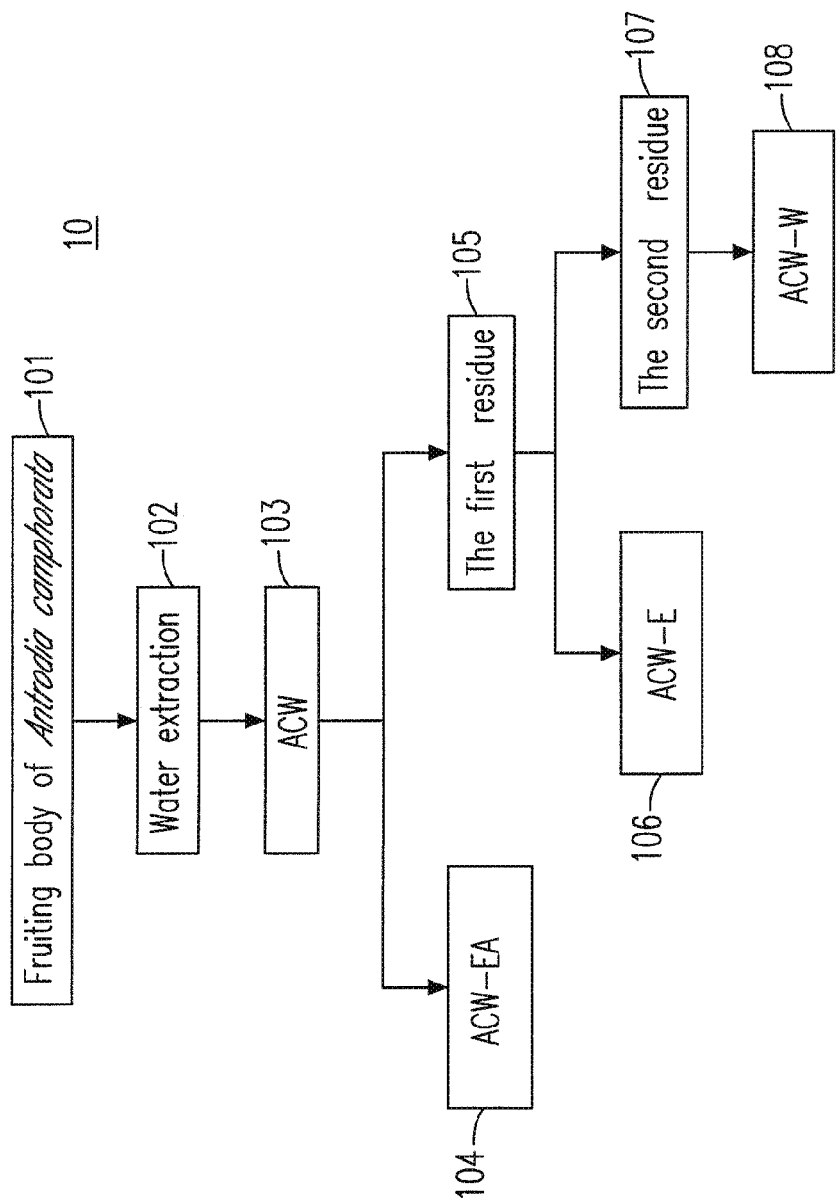
FIG. 3 is a flowchart showing the preparing method of ACW and the subsequent organic solvent extracts and a second water extract in the first preferred embodiment of the present invention.

2. Immunostimulatory Activity of Subfraction from ACW on Phenotypic Maturation of DCs Polysaccharide is further identified as the major bioactive component of ACW for inducing cellular maturation. Please refer to FIG. 3, which is a flowchart showing the preparing method of ACW and the subsequent organic solvent extracts and a second water extract in the first preferred embodiment of the present invention. First, the wild fruiting bodies of AC (step 101) is extracted with water (step 102) to obtain a water extract of the fruiting body of A. camphorate (ACW) (step 103). Next, ACW is extracted with ethyl acetate to obtain ethyl acetate extract of the fruiting body of A. camphorata (ACW-EA) (step 104) and a first residue (step 105), and then the first residue is extracted with ethanol to obtain an ethanol extract of the fruiting body of A. camphorata (ACW-E) (step 106) and a second residue (step 107). Finally, the second residue is extracted with water to obtain a second water extract of the fruiting body of A. camphorata (ACW-W) (step 108).

Yields of ACW-EA, ACW-E and ACW-W respectively are 8.9%, 38.5% and 52.6% of the weight of ACW.

Figure 4:
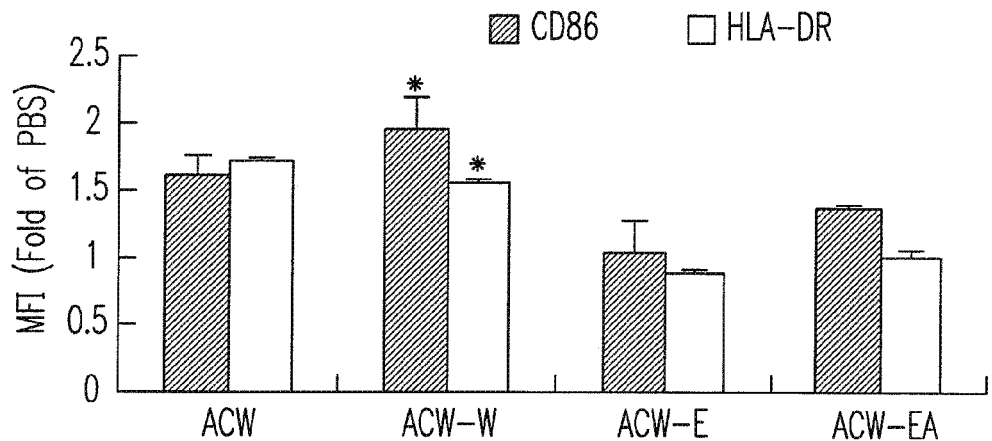
FIG. 4 is a diagram showing expressions of CD86 and HLA-DR after ImDCs are stimulated with the respective extracts of AC.

Subsequently, ImDCs are stimulated with ACW and its fractionized extracts respectively. DCs treated with ACW or ACW-W increase the expressions of CD86 (1.6- and 1.9-fold) and HLA-DR (1.5- and 1.7-fold) compared with the control (PBS). However, the expressions of CD86 and HLA-DR of DCs induced by ACW-E and ACW-EA respectively are obviously less than those induced by ACW-W or ACW (FIG. 4).

Figure 5:
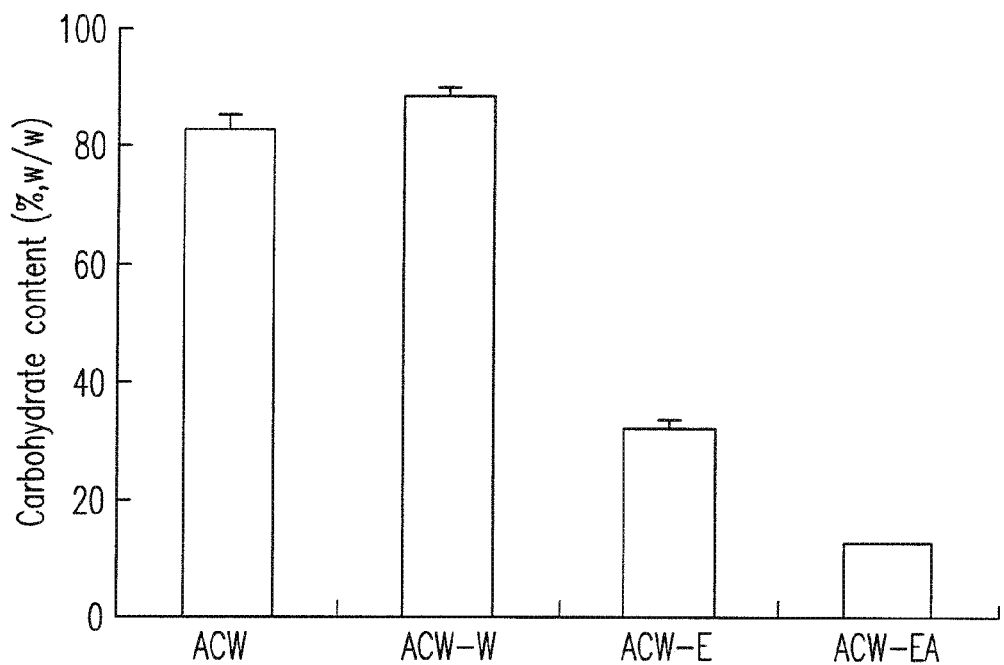
FIG. 5 is a bar chart showing the carbohydrate content of the respective extracts of AC.

The carbohydrate content in ACW and the subsequent fractionized extracts are further analyzed with phenol-sulfuric acid method. The carbohydrate content in ACW-W is the most abundant (88.2%), compared to 31.8% and 12.9% in ACW-E and ACW-EA, respectively (FIG. 5).

The following characteristics can be observed by the analysis of $^1$H NMR spectra of ACW and its fractionized extracts. The experimental conditions of $^1$H NMR spectrum are: the equipment with resolution of 600 MHz, and concentration of 10.0 mg/0.75 ml. ACW and ACW-W are solved in $D_2O$, and ACW-EA and ACW-E with lower polarity are solved in $C_5D_5N$ for comparison.

Figure 6A:
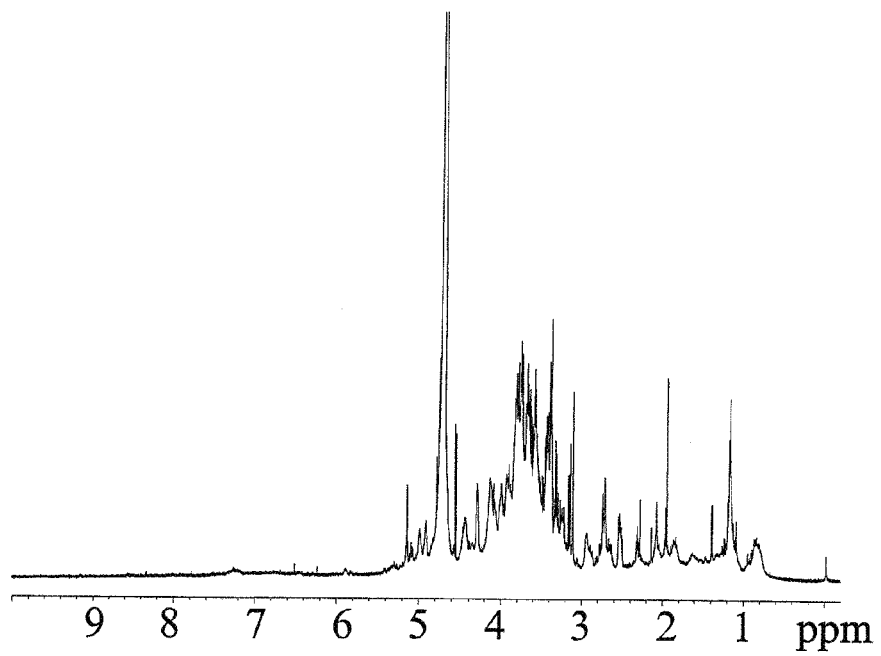
FIGS. 6(A) to 6(D) are the diagrams showing $^1$H NMR spectra of (A) ACW, (B) ACW-EA, (C) ACW-E and (D) ACW-W.
Figure 6B:
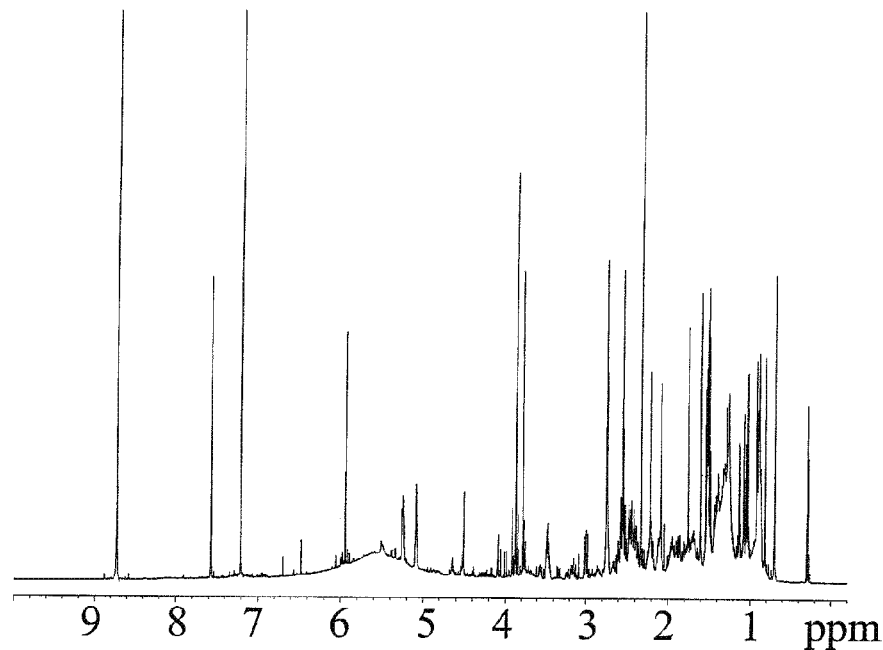
Figure 6C:
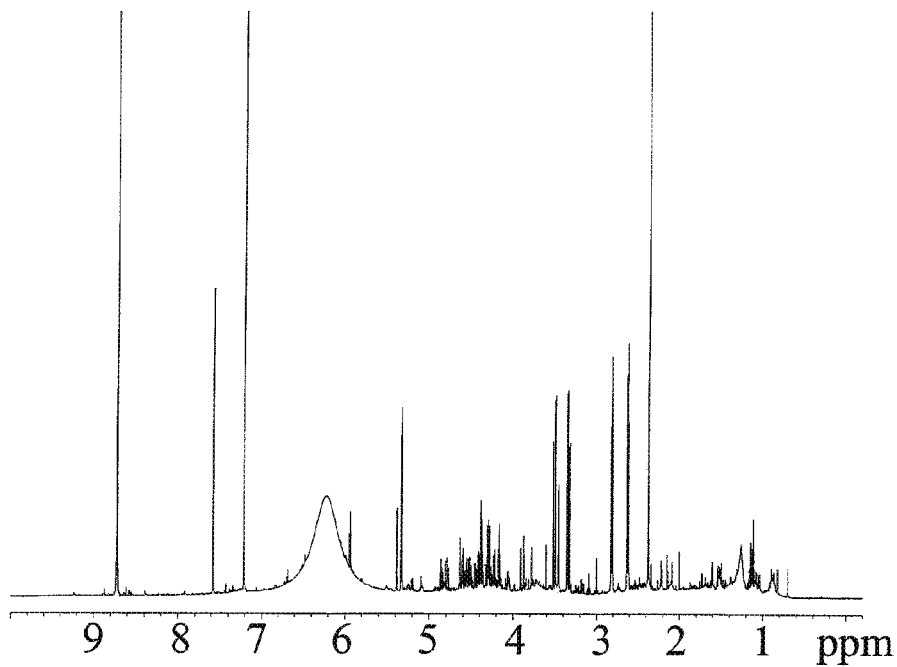
Figure 6D:
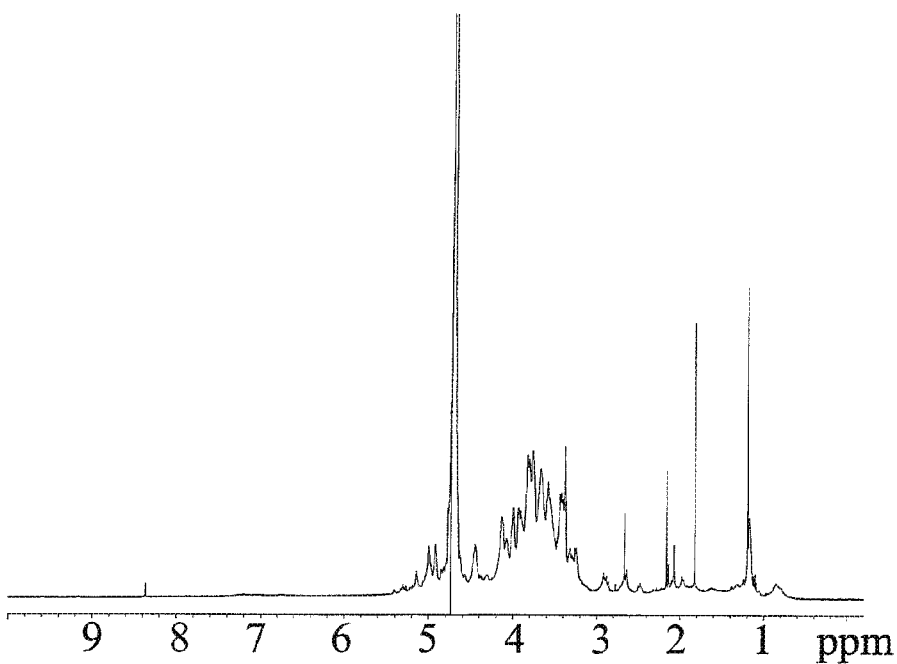
Figure 6E:
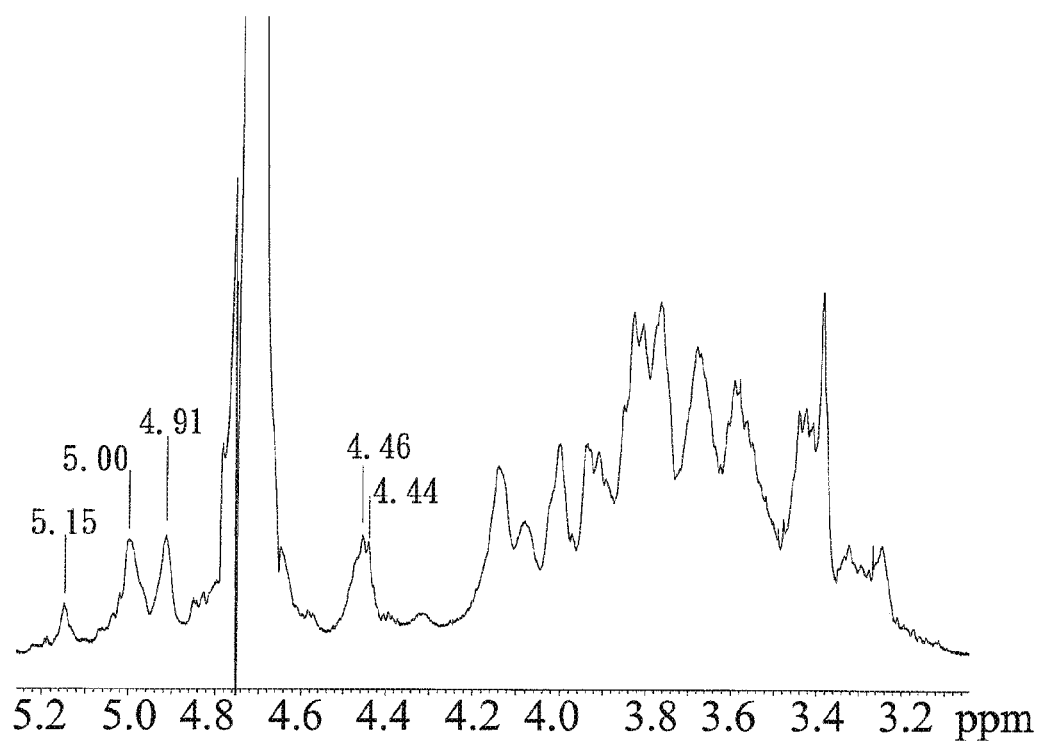
FIG. 6(E) is a diagram showing a locally amplified $^1$H NMR spectrum of ACW-W.

Please refer to FIGS. 6(A) to 6(D), which are the diagrams showing $^1$H NMR spectra of (A) ACW, (B) ACW-EA, (C) ACW-E and (D) ACW-W. When $^1$H NMR spectra of FIGS. 6(A) to 6(D) are partially merged and compared, it can be found that ACW-W has the highest ratio of carbohydrate signals ranged between 3.0 and 5.5, and the specific hydrogen signals of anomeric carbons of the polysaccharides at 4.44, 4.46, 4.91, 5.00 and 5.15 ppm (FIG. 6(E)).

Figure 7:
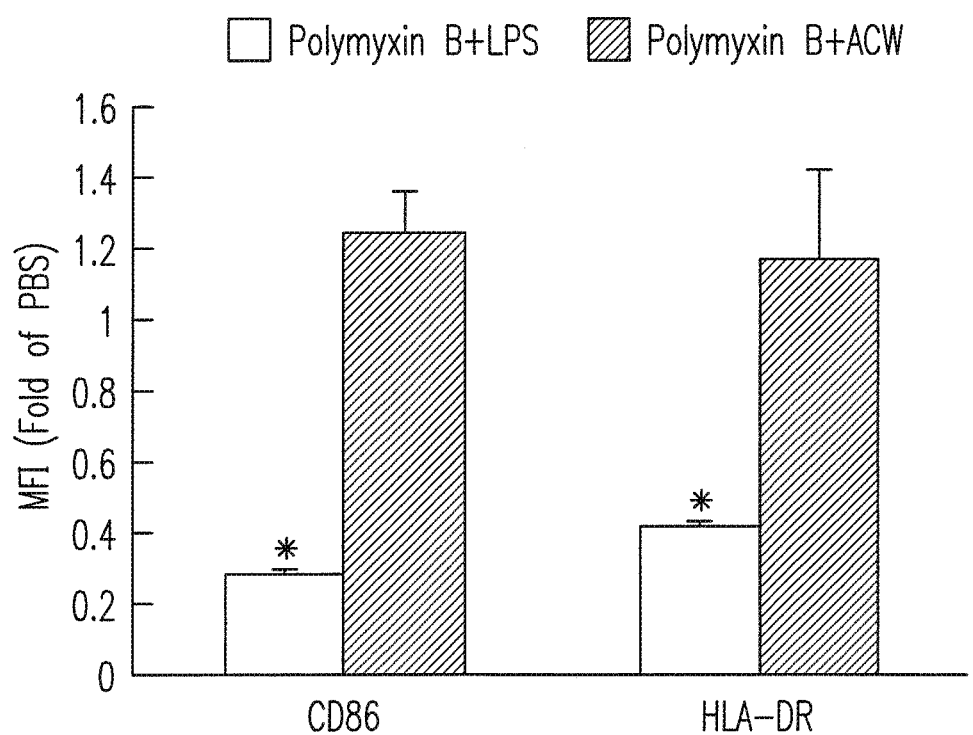
FIG. 7 is a diagram showing expressions of CD86 and HLA-DR induced by treating DCs with polymyxin B in advance and then with LPS or ACW.

In addition, polymyxin B test identifies that ACW indeed can induce the maturation of DCs, and this activity does not originate from LPS contamination. Polymyxin B is an antibiotic used for inactivating potential LPS contamination when evaluating the activity of different agents on immune cells. Therefore, whether polymyxin B blocks the phenotypic maturation of ACW-induced DCs is determined. The results show that polymyxin B accelerates an increased expressions of CD86 and HLA-DR by ACW, but significantly inhibits the expressions of CD86 and HLA-DR on LPS-induced DCs (FIG. 7). Accordingly, ACW is able to stimulate the maturation of DCs without LPS contamination.

Figure 8:
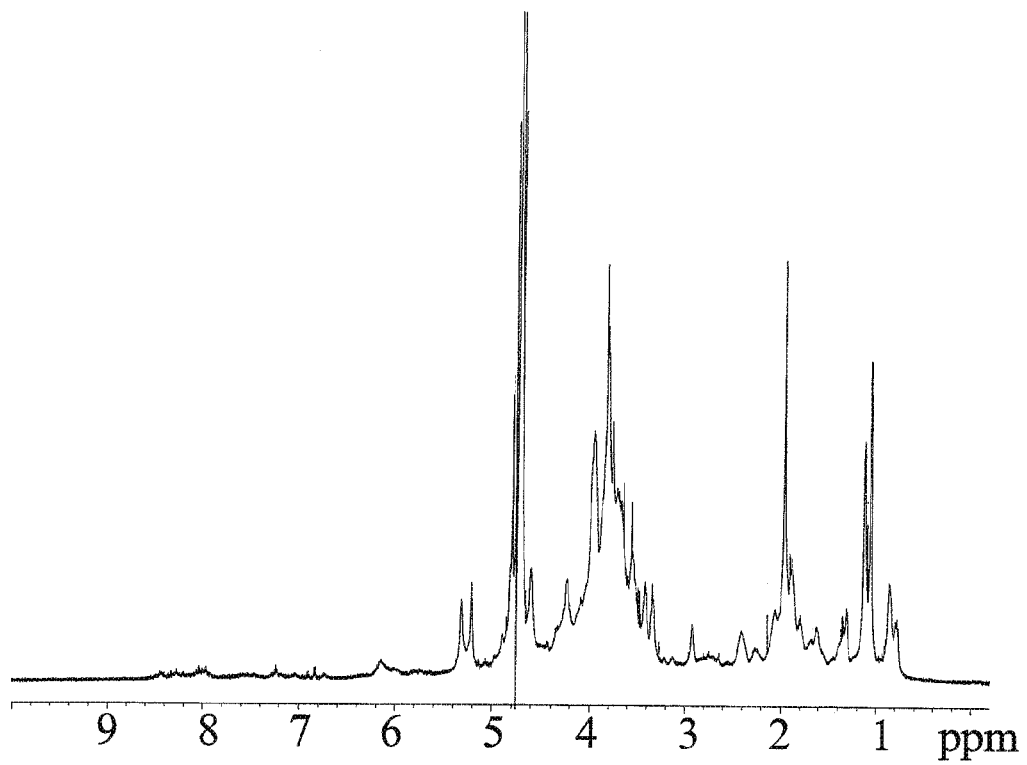
FIG. 8 is a $^1$H NMR spectrum of LPS.

Further, ACW-W and LPS are compared at the identical conditions with $^1$H NMR spectrum. It can be found that ACW-W almost only has signal characteristic of carbohydrate when merging and comparing FIG. 6(D) with FIG. 8, and does not show long-chain signals of LPS at 0.70 to 2.40 ppm. Therefore, the second water extract (ACW-W) with characteristic $^1$H NMR signals of polysaccharides has mainly contribution to the immunostimulatory activity of ACW in causing the maturation of dendritic cells.

From the above-mentioned experimental results, it is concluded that the inducing immune activity of ACW was identified as polysaccharides.

3. Effect of ACW on the Functional Maturation of DCs

Figure 9:
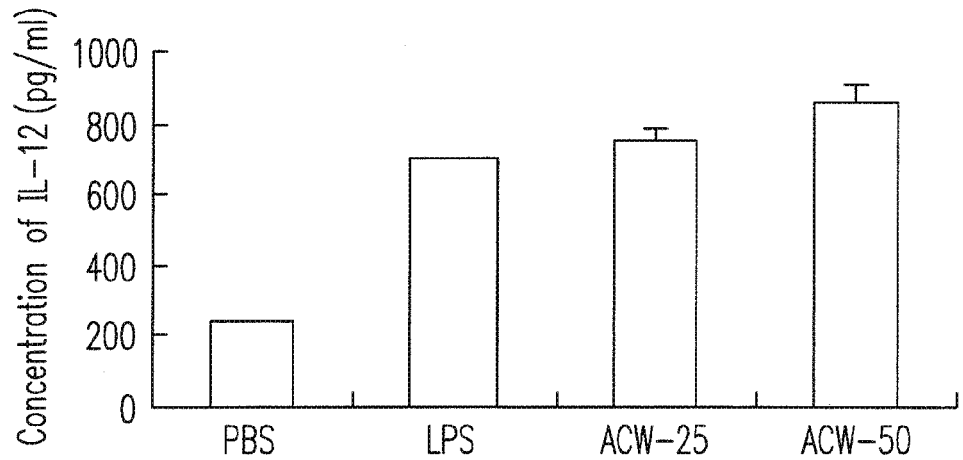
FIG. 9 is a diagram showing the interleukin-12 (IL-12) produced from induction of DCs with different concentrations of ACW.

Stimulation of DCs induces the production of a wild range of cytokines. Cytokine production of DCs plays an integral role in activating naive T cells, wherein IL-12 is a DC-derived factor that directs the development of T helper 1 (Th1) cells, producing high levels of IFN-γ. Please refer to FIG. 9, which is a diagram showing IL-12 produced from induction of DCs with different concentrations of ACW. In FIG. 9, the ability of ACW (25 μg/ml and 50 μg/ml) to stimulate DCs and produce IL-12 is stronger than that of LPS, and the determined concentration of IL-12 are 235.53±2.54 (PBS), 698.45+5.46 (LPS), 758.14+26.54 (ACW-25) and 855.7±56.21 (ACW-50) μg/ml.

Figure 10:
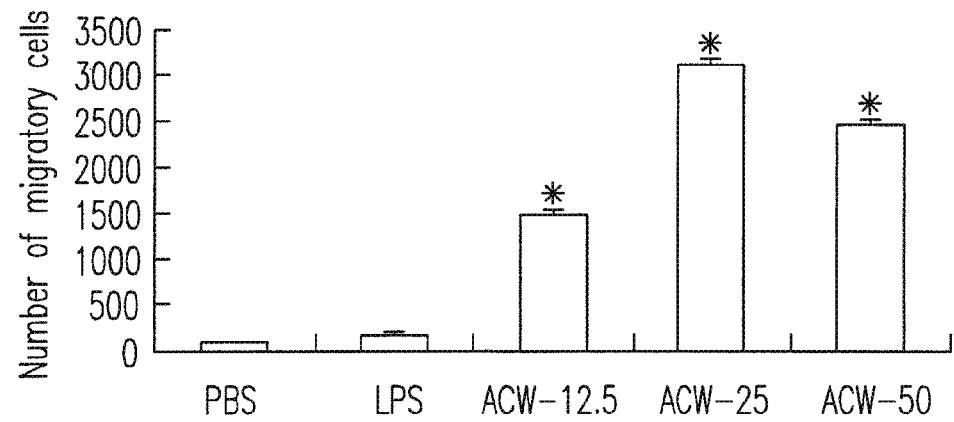
FIG. 10 is a diagram showing the migratory ability of ImDCs stimulated with different concentrations of ACW.

IL-12 acts a chemoattractant for macrophages and is required for DC migration. Please refer to FIG. 10, which is a diagram showing the migratory ability of ImDCs stimulated with different concentrations of ACW. In FIG. 10, comparing with PBS and LPS, the stimulation of different ACW (12.5, 25 and 50 μg/ml) on ImDCs is able to effectively induce the migration of DCs, wherein the maximal cell migration to ACW is generated at 25 μg/ml ACW and 50 μg/ml ACW produces a diminished migratory response.

Figure 11A:
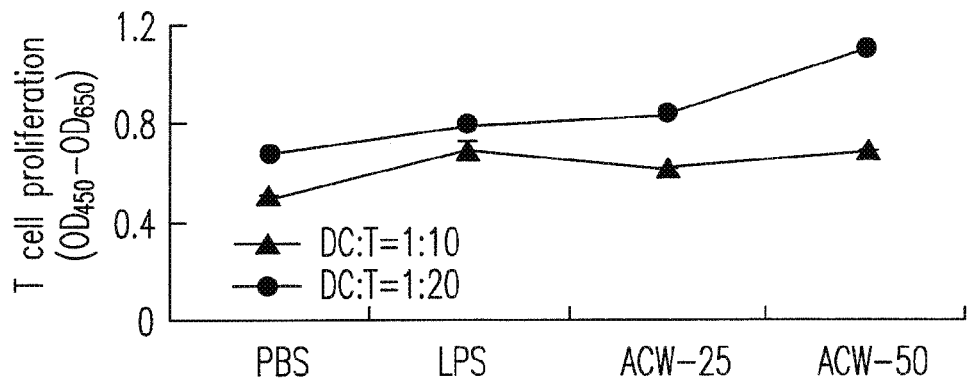
FIG. 11(A) is a diagram showing the relationship of T cell proliferation and different concentrations of ACW at different DCs/T cells ratios.
Figure 11B:
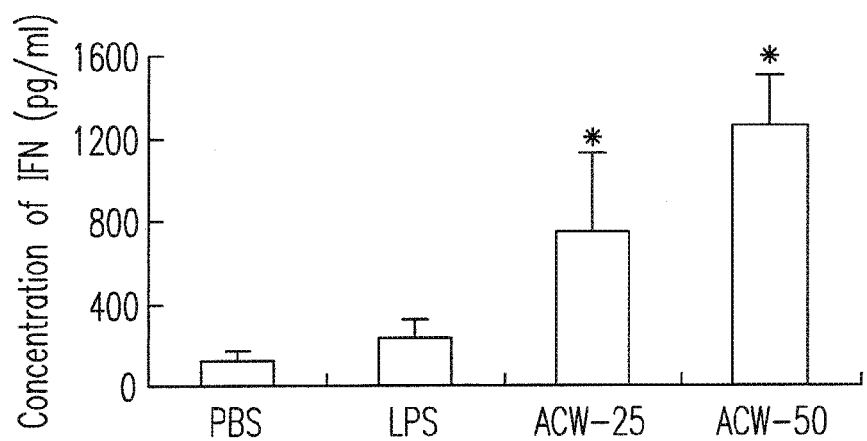
FIG. 11(B) is a diagram showing IFN-γ production by stimulating DCs and activating helper T cells at different concentrations of ACW.

DCs efficiently present antigens to T cells and can polarize T cell differentiation depending on their phenotype. Please refer to FIG. 11(A), which is a diagram showing the relationship of T cell proliferation and different concentrations of ACW at different DCs/T cells ratios. In FIG. 11(A), comparing with PBS and 100 ng/ml LPS, 25 and 50 μg/ml ACW can efficiently stimulate DCs and activate T cells. Please refer to FIG. 11(B), which is a diagram showing IFN-γ produced by stimulating DCs and activating helper T cells at different concentrations of ACW. In FIG. 11(B), comparing with PBS and LPS, 25 and 50 μg/ml ACW can efficiently stimulate DCs, activate helper T cells and efficiently increase the production of IFN-γ induced by helper T cells. It can be known from the above results that ACW is able to induce DCs to produce abundant IFN-γ and ACW-induced DCs are able to induce naive T cells to Th1 pathways.

4. Effect of ACW on Cell Survival in the Maturation Process of DCs

Figure 12A:
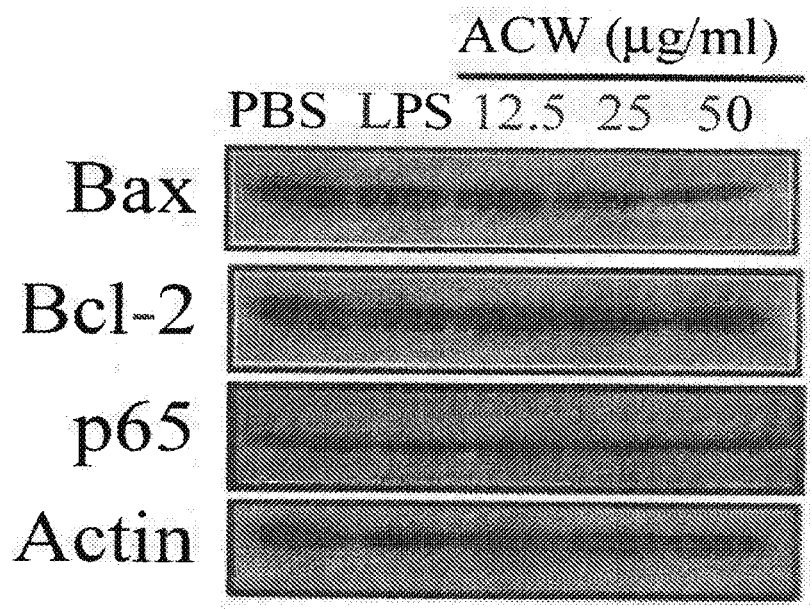

Induction of apoptosis is one of the escape mechanism of tumor cells from the immune surveillance system, while apoptotic inhibition of DCs enhances the antigen-specific immune response. Therefore, it needs to determine the cytotoxicity of ACW to DCs. It is found that more than 90% of the cells exhibit the characteristic phenotypes of mature DCs after the stimulation with ACW on day eight. ACW is not cytotoxic to DCs after long-term incubation. In addition, ACW treatment on DCs can dramatically decrease Bax expression, whereas increase Bcl-2 and NFκB p65 expressions (FIG. 12(A)).

Figure 12B:
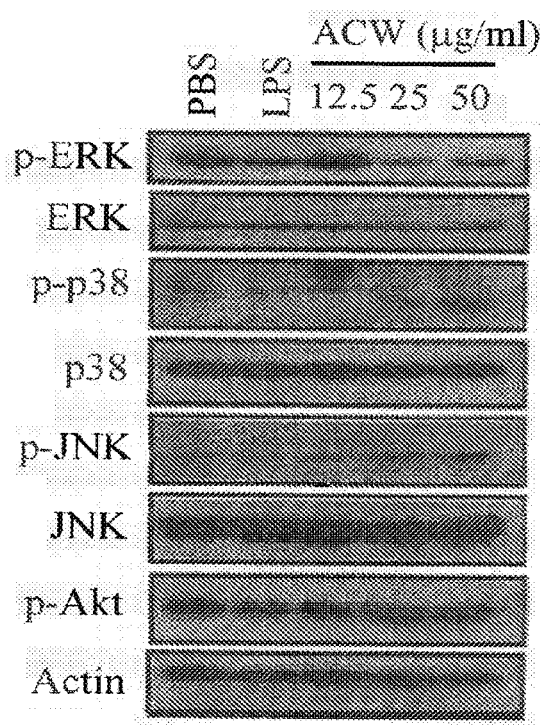

5. Critical Roles of Akt and MAPKs in Regulating the Functional Maturation of DCs Induced by ACW The maturation and functions of DCs relates to PI3K/Akt and MAPKs signaling transduction pathways. The cellular signaling transduction pathways of the ACW-stimulated DCs are further identified. Please refer to FIG. 12(B), which is the diagram showing protein expressions of signaling transduction pathway of the ACW-stimulated DCs. In FIG. 12(B), comparing with PBS and LPS, higher levels of p-p38, p-JNK and p-Akt are activated in DCs treated with 25 and 50 μg/ml ACW. In addition, higher levels of p-ERK is activated in DCs treated with 12.5 μg/ml ACW, but significantly declined with higher doses of ACW. The levels of nonphosphorylated ERK remains stable in different concentrations of ACW.

Figure 13A:
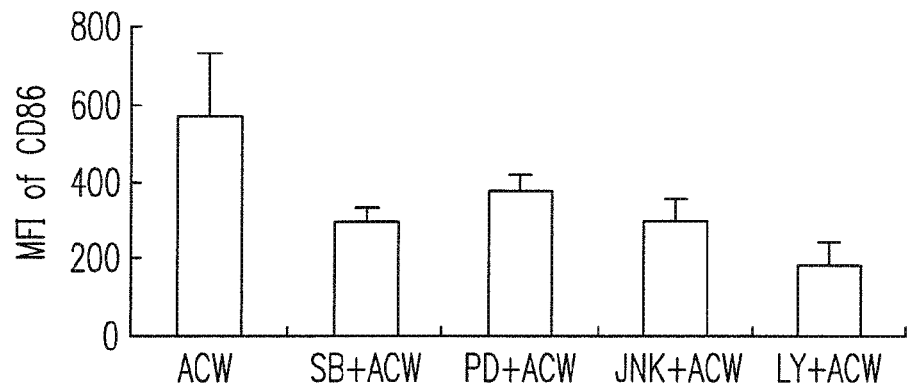
FIGS. 13(A) and 13(B) respectively are the diagrams showing expressions of (A) CD86 and (B) IL-12 after DCs are inhibited by signaling transduction pathway protein inhibitors and then treated with ACW.
Figure 13B:
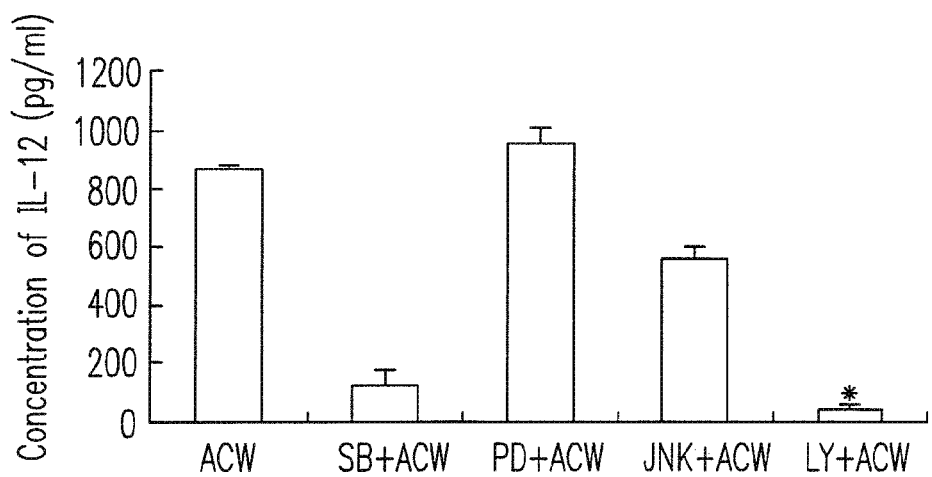

To analyze the relationship between PI3K and MAPKs signaling transduction pathways of DCs, DCs are pretreated with the inhibitors (SB203580, PD98059, SP600125 and LY294002, respectively) to inhibit the activation of p38, ERK1/2, JNK, PI3K, and then are stimulated with ACW. The results show that p38 (SB203580), JNK (SP600125) and Akt (LY294002) are able to inhibit CD86 expression of the ACW-treated DCs (FIG. 13(A)). Furthermore, inhibition of p38 and Akt significantly blocks the up-regulation of IL-12 production of DCs induced by ACW. The ERK inhibitor (PD98059) upregulates the IL-12 production by DCs in response to ACW (FIG. 13(B)). Taken together, it is concluded that ACW induces the activation of Akt and p38 leading to the differentiation and functional maturation of DCs.

Comparing with GLW and ABW, ACW has better ability for inducing the maturation of DCs. ACW is able to induce the maturation of DCs via the activation of PI3K/Akt and p38/MAPKs signaling transduction pathways, enhances T cell proliferation and IFN-γ production, and polarizes them toward the Th1 pathway. ACW further enhances DC survival by inhibiting apoptotic pathways. Accordingly, ACW is able to applied in cancer immunotherapy.

The extracts obtained from ACW sequentially extracted with ethyl acetate, ethanol and water can be found that the carbohydrate contents therein influences the level of DC activation, and demonstrates that the inducing immune components of ACW are originated from polysaccharides.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for preparing an ethanol extract of a fruiting body of an *Antrodia camphorata*, comprising the steps of:
    (a) providing the fruiting body;
    (b) boiling the fruiting body in water to obtain a water extract having a precipitate therein;
    (c) removing the precipitate from the water extract;
    (d) extracting the water extract with ethyl acetate to obtain an ethyl acetate extract and a first residue;
    (e) extracting the first residue with ethanol to obtain an ethanol extract and a second residue; and
    (f) separating the second residue from said ethanol extract.

2. The method according to claim 1, wherein the step (a) further comprises a step (a1) of grinding the fruiting body as a powder.

3. The method according to claim 1, wherein the step (b) further comprises a step (b1) of refluxing the water extract after the boiling step.

4. The method according to claim 1, wherein the step (c) is performed by at least one of treatments of filtering the water extract and centrifuging the water extract.

5. A method for preparing an aqueous extract of a fruiting body of an *Antrodia camphorata*, comprising the steps of:
    (a) providing the fruiting body;
    (b) boiling the fruiting body in water to obtain a water extract having a precipitate therein;
    (c) removing the precipitate from the water extract;
    (d) extracting the water extract with ethyl acetate to obtain an ethyl acetate extract and a first residue;
    (e) extracting the first residue with ethanol to obtain an ethanol extract and a second residue; and
    (f) extracting the second residue with water to obtain said aqueous extract.

* * * * *